United States Patent [19]
Mowry et al.

[11] Patent Number: 5,567,860
[45] Date of Patent: Oct. 22, 1996

[54] HIGH PURITY TERTIARY OLEFIN PROCESS USING REMOVAL OF SECONDARY ETHERS

[75] Inventors: John R. Mowry, Mount Prospect, Ill.; Jacqueline A. Harris, Ash, England; Charles P. Luebke, Mount Prospect; David A. Hamm, Hinsdale, both of Ill.

[73] Assignee: UOP, Des Plaines, Ill.

[21] Appl. No.: 317,947

[22] Filed: Oct. 4, 1994

Related U.S. Application Data

[63] Continuation-in-part of Ser. No. 928,584, Aug. 13, 1992, abandoned.

[51] Int. Cl.$^6$ .............................. C07C 1/00; C07C 41/00
[52] U.S. Cl. .......................... 585/639; 585/324; 585/638; 585/640; 568/697
[58] Field of Search ...................... 585/638, 639, 585/640, 324

[56] References Cited

U.S. PATENT DOCUMENTS

| | | | |
|---|---|---|---|
| 4,287,379 | 9/1981 | Brunner et al. | 585/839 |
| 4,320,232 | 3/1982 | Volkamer et al. | 568/697 |
| 4,570,026 | 2/1986 | Keyworth et al. | 585/312 |

FOREIGN PATENT DOCUMENTS

| 0202881 | 1/1966 | U.S.S.R. | 116/260 |
|---|---|---|---|

OTHER PUBLICATIONS

Dr. Fritz Obenaus et al, "Huels Process: Methyl Tertiary Butylether" ALCHE 85th National Meeting, Phil., Jun. 4, 1978.
Ullmann's Encyclopedia of Industrial Chemistry, vols. A4 & A16, 5th Edition (VCH, Weinheim, Germany).
"Hydrocarbon Processing", Aug. 1981, p. 101.
"Hydrocarbon Processing", Dec. 1979, p. 109.

*Primary Examiner*—Ponnathapura Achutamurthy
*Attorney, Agent, or Firm*—Thomas K. McBride; John J. Tolomei; Michael A. Moore

[57] ABSTRACT

A process for the production of $R_2$-isoolefins by decomposition of $R_1$—O—tertiary-$R_2$ is disclosed. $R_1$—O—secondary-$R_2$ that are normally present in the feed stream are selectively removed. Removal of these $R_1$—O—secondary-$R_2$ lowers the $R_2$-normal olefin impurity and increases the yield of the product $R_2$-isoolefins.

27 Claims, 1 Drawing Sheet

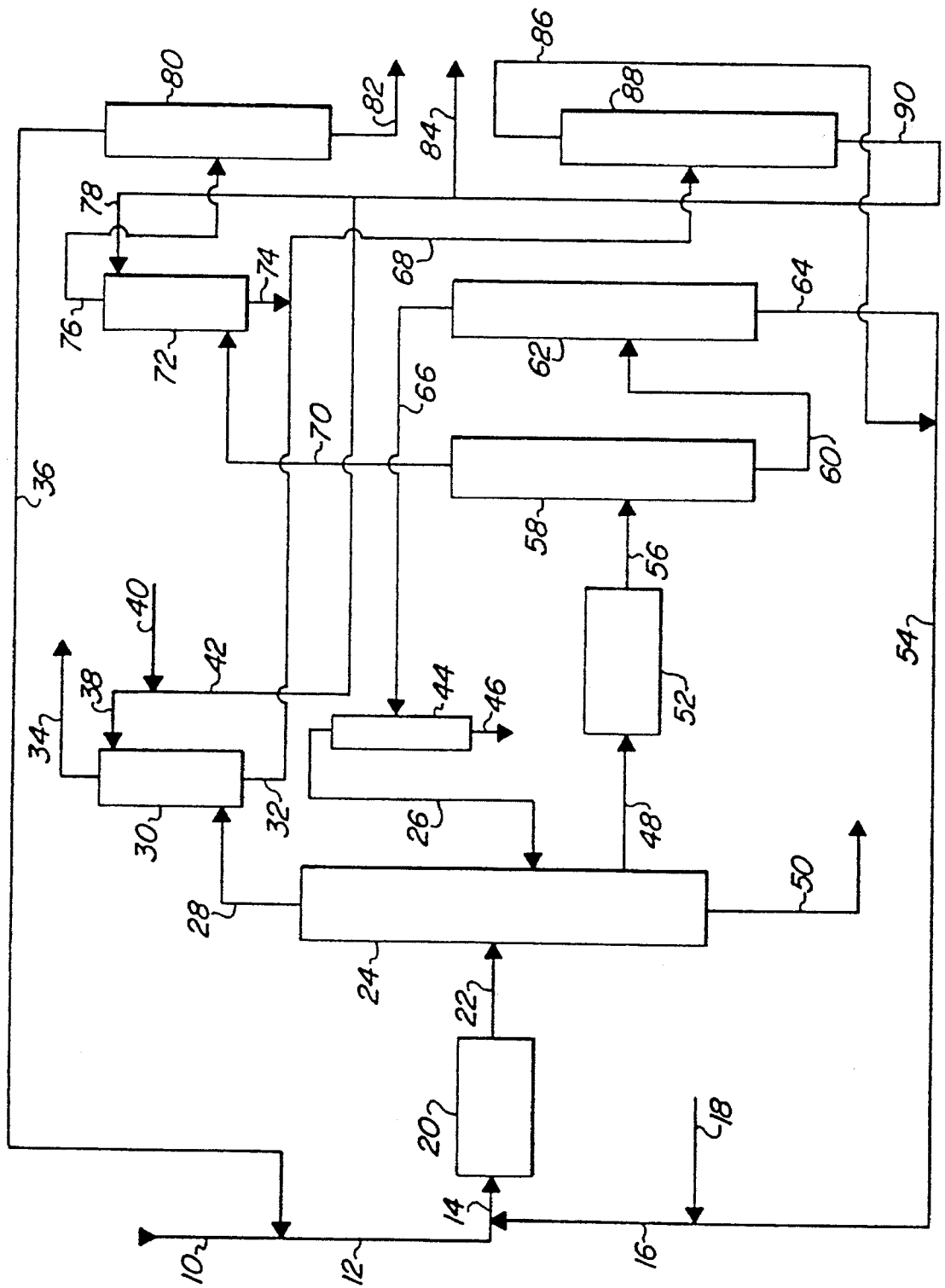

HIGH PURITY TERTIARY OLEFIN PROCESS USING REMOVAL OF SECONDARY ETHERS

CROSS REFERENCE TO RELATED APPLICATION

This is a continuation-in-part of prior application Ser. No. 928,584, filed Aug. 13, 1992, now abandoned.

FIELD OF THE INVENTION

This invention is a process for the production of high purity isoolefins.

BACKGROUND OF THE INVENTION

Over fifty years ago it was recognized that synthetic butyl rubber was a quite effective substitute to natural rubber in many respects. Because of its low price, its temperature stability, and its effectiveness in a wide range of rubber formulations, butyl rubber rapidly displaced natural rubber in automobile tire applications and became widely used in household and industrial products. Today, butyl rubber, polyisobutylene, and other polymers of isobutene are produced in a wide range of high-molecular weight, elastomeric grades.

Nearly thirty years ago it became apparent that isobutene made by decomposing alkyl tertiary-butyl ethers met the purity requirements of commercial polymerization-grade isobutene. However, these alkyl tertiary-butyl ethers remained in short supply until the last decade when, as environmental pressures over anti-knock additives in gasoline increased, production of these alkyl tertiary-butyl ethers by etherifying mixed butenes boomed, and a concomitant search for a decomposition process followed. Two of the chief criteria for a decomposition process are yield and impurity.

Yield is defined as the percentage of total alkyl tertiary-butyl ether in the feed which appears as isobutene in the product and can be expressed by the equation:

$$Y=P/F*100$$

where Y equals percent yield, P equals moles of isobutene in the product, and F equals moles of alkyl tertiary-butyl ether in the feed. The higher the yield, the more desirable is the process.

High purity is a major requirement of isobutene feedstocks used for polymerization. This was also the case when butyl rubber was first produced, because of requirements on molecular weight and heat and chemical resistance. Today's high-molecular weight grades of butyl rubber and polyisobutylene require a commercial polymerization-grade isobutene of >99.5 wt% purity with impurity limits for isobutane, propylene, pentenes, oxygenated compounds, and water, but as used herein the term "impurity" is intended to indicate a concentration of total normal butenes in parts per million by weight in the isobutene product.

Consequently, the ideal process is one where the yield equals 100 and the impurity equals zero. The minimum requirement is that yield be at least 92% and impurity be not more than 500 ppm by weight. These are minimum requirements; that is, if a process fails to meet these requirements simultaneously the process is commercially unacceptable. The impurity requirement is assuming added importance and significance in view of the expectation in some areas of minimum standards for impurity in isobutene of not more than 300 ppm by weight near-term.

The isolation of isobutene from mixtures of $C_4$ hydrocarbons by the combined process of etherifying isobutene and subsequently decomposing methyl tertiary-butyl ether (MTBE) is well known and described in the paper authored by Fritz Obenaus et al. entitled "Huels Process: Methyl Tertiary Butylether", presented at the AIChE 85th National Meeting in Philadelphia, Jun. 4–8, 1978 and in the article starting at page 109 of the December 1979 issue of "Hydrocarbon Processing." The individual processes of olefin etherification and ether decomposition for $C_4$ hydrocarbons are described in "Ullmann's Encyclopedia of Industrial Chemistry," Volumes A4 and A16, Fifth Edition (VCH, Weinheim, Germany).

Flow schemes for the combined process of olefin etherification and ether decomposition with means to decrease the contaminants in the isobutene product are well known. U.S. Pat. No. 4,570,026 and the article starting at page 101 of the August 1981 issue of "Hydrocarbon Processing" describe recycling by-products with unreacted MTBE from a decomposition section to an etherification section, and ultimately bleeding out the by-products from upstream of the decomposition section in an intermediate product stream of MTBE. Where there is no intermediate product stream of MTBE, the August 1981 "Hydrocarbon Processing" reference suggests removing the by-products using a "recycle purification unit" on the MTBE recycle stream between the decomposition section and the etherification section; however, what the "recycle purification unit" comprises is not described. U.S. Pat. No. 4,287,379 and U.S. Pat. No. 4,320,232 teach purging out the by-products via an alcohol-containing stream from either the side of a distillation column downstream of the decomposition reactor or from the alcohol recycle stream between the decomposition section and the etherification section.

BRIEF SUMMARY OF THE INVENTION

This invention is a process that increases the purity and yield of $R_2$-isoolefins obtained via decomposition of $R_1$—O-tertiary-$R_2$ by providing a particularly effective separation system for the removal of $R_1$—O-secondary-$R_2$ isomers. As a result, $R_1$—O-secondary-$R_2$ that is normally present in a recycle stream that arises from the decomposition of $R_1$—O-tertiary-$R_2$ is selectively separated, at least in pan, prior to the stream being recycled to either an etherification section or the decomposition section. This invention not only lowers the impurity of the product $R_2$-isoolefin but also increases the $R_2$-isoolefin yield.

This invention has two broad embodiments. In a first embodiment, this invention is a process for producing $R_2$-isoolefins, where $R_2$ is either a $C_4$ or a $C_5$ alkyl group. The feed stream for the process comprises $R_1$—O-tertiary-$R_2$ and $R_1$—O-secondary-$R_2$ and has a first ratio of $R_1$—O-tertiary-$R_2$/$R_1$—O-secondary-$R_2$. $R_1$ is an alkyl group comprising from 1 to 5 carbon atoms. The feed stream is passed into a decomposition zone maintained at first decomposition conditions effective to decompose the $R_1$—O-tertiary-$R_2$ to the $R_2$-isoolefin that corresponds to the $R_2$. A decomposition effluent stream is recovered from the decomposition zone. The decomposition effluent stream comprises the $R_2$-isoolefin and the $R_1$—O-secondary-$R_2$. At least a portion of the decomposition effluent stream is passed into a first separation zone that is operated at conditions effective to separate the portion of the decomposition effluent stream into a product stream and a first recycle stream. The product stream comprises the $R_2$-isoolefin and the first recycle stream comprises the $R_1$—O-secondary-$R_2$. The first recycle stream has a second ratio of $R_1$—O-tertiary-$R_2$/$R_1$—O-secondary-$R_2$ that is less than the first ratio. At least a portion of the first recycle stream is passed into a second separation zone that is operated at conditions effective to selectively separate the portion of the first recycle stream into a drag stream and a second recycle stream. The drag stream has a first concentration of the $R_1$—O-secondary-$R_2$, and the second recycle stream has a second concentration of the $R_1$—O-secondary-$R_2$ that is less than the first concentration. At least a portion of the second recycle stream is recycled to the decomposition zone. The drag stream is withdrawn from the process.

In a more limited embodiment, this invention is a process for obtaining isobutene from a $C_4$ hydrocarbon mixture comprising isobutene. A $C_4$ hydrocarbon mixture comprising isobutene and an $R_1$—OH is passed into an etherification zone maintained at etherification conditions effective to etherify the isobutene. $R_1$ is an alkyl group comprising from 1 to 5 carbon atoms. An etherification effluent stream is recovered from the etherification zone. The etherification effluent stream comprises $C_4$ hydrocarbons, an $R_1$—O-tertiary-$C_4$ corresponding to the $R_1$, and an $R_1$—O-secondary-$C_4$ corresponding to the $R_1$. At least a portion of the etherification effluent stream is passed into a first separation zone operated at conditions effective to separate the portion of the etherification effluent stream into a first product stream and an etherification product stream. The first product stream comprises $C_4$ hydrocarbons and the etherification product stream comprises the $R_1$—O-tertiary-$C_4$ and the $R_1$—O-secondary-$C_4$. The etherification product stream has a first ratio of $R_1$—O-tertiary-$C_4$/$R_1$—O-secondary-$C_4$. At least a portion of the etherification product stream is passed into a decomposition zone that is maintained at first decomposition conditions effective to decompose the $R_1$—O-tertiary-$C_4$ to isobutene. A decomposition effluent stream comprising isobutene and the $R_1$—O-secondary-$C_4$ is recovered from the decomposition zone. At least a portion of the decomposition effluent stream is passed into a second separation zone that is operated at conditions effective to separate the portion of the decomposition effluent stream into a second product stream and a first recycle stream. The second product stream comprises isobutene and the first recycle stream comprises the $R_1$—O-secondary-$C_4$. The first recycle stream has a second ratio of $R_1$—O-tertiary-$C_4$/$R_1$—O-secondary-$C_4$ that is less than the first ratio. At least a portion of the first recycle stream is passed into a third separation zone that is operated at conditions effective to selectively separate the portion of the first recycle stream into a first drag stream and a second recycle stream. The first drag stream has a first concentration of the $R_1$—O-secondary-$C_4$ and the second recycle stream has a second concentration of the $R_1$—O-secondary-$C_4$ that is less than the first concentration. At least a portion of the second recycle stream is recycled to either the etherification zone, the first separation zone, and the decomposition zone. The first drag stream is withdrawn from the process.

BRIEF DESCRIPTION OF THE DRAWING

FIG. 1 is a simplified process flow diagram of a process for the isolation of isoolefins from a mixture of hydrocarbons arranged in accord with a preferred embodiment of the invention.

DETAILED DESCRIPTION OF THE INVENTION

It is well known that isoolefins produced by olefin etherification and ether decomposition are contaminated by normal olefins of the same carbon number. The $R_2$-normal olefins that contaminate an $R_2$-isoolefin product principally arise from two components in the feed to the decomposition zone, $R_2$-normal olefins and $R_1$—O-secondary-$R_2$. These components contribute in different proportions to the contamination problem. Whereas essentially all of the $R_2$-normal olefins that enter the decomposition zone generally pass through unreacted and ultimately contaminate the $R_2$-isoolefin product, generally not more than about 10–15% by weight of the $2NR_1$—O-secondary-$R_2$ that enters the decomposition zone decomposes to $R_2$-normal olefins. However, the contribution by this $R_1$—O-secondary-$R_2$ looms large where the $R_2$-normal olefins that enter the decomposition zone are reduced but the impurity requirement for the $R_2$-isoolefin product is not met. A process which eliminates or significantly reduces the $R_1$—O-secondary-$R_2$ entering the decomposition zone is useful because it can not only reduce the $R_2$-normal olefin impurity but also increase the yield of the $R_2$-isoolefin product.

$R_1$ and $R_2$ designate the specific radicals that are most useful for this invention. "$R_1$—OH" is either an alcohol containing from 1 to 5 carbon atoms and at least one hydroxyl group, such as methanol, ethanol, propanols, ethylene glycol, and propylene glycol, or water. "$R_1$" is the group resulting from the loss of one hydroxyl group from an $R_1$—OH, such as a methyl group, an ethyl group, a normal propyl group, an isopropyl group, a hydroxy-ethyl group, a (hydroxy)-normal propyl group, or a hydrogen free radical. "$R_2$" is an alkyl group containing from 4 to 5 carbon atoms, such as a butyl group or a pentyl group.

In the first embodiment of the invention, the feed stream to the decomposition zone contains principally an $R_1$—O-tertiary-$R_2$. The feed is generally 99.5% by weight or greater $R_1$—O-tertiary-$R_2$, and preferably 99.8% by weight or greater $R_1$—O-tertiary-$R_2$. The remainder of the feed may be $R_2$-isoolefin, $R_2$-normal olefin, and $R_2$-oligomers (mainly $R_2$-dimers). Preferably, the feed stream is virtually free from $R_1$—OH. The feed stream will also contain $R_1$—O-secondary-$R_2$. The feed stream may be obtained, for example, by etherification of the $R_2$-isoolefins in a stream of mixed $R_2$-hydrocarbons with an $R_1$—OH, and subsequently removing by distillation $R_2$-hydrocarbons and $R_1$—OH.

Where the feed stream is obtained by olefin etherification processes of the prior art, the feed stream may contain generally from about 300 to about 800 ppm by weight $R_1$—O-secondary-$R_2$. The relative concentrations of the $R_1$—O-tertiary-$R_2$ and of the $R_1$—O-secondary-$R_2$ can also be referred to in terms of a ratio of $R_1$—O-tertiary-$R_2$/$R_1$—O-secondary-$R_2$. The feed stream, therefore, contains a relatively high ratio of $R_1$—O-tertiary-$R_2$/$R_1$—O-secondary-$R_2$. Where the $R_2$-normal olefin impurity requirement of the $R_2$-isoolefin product is stringent, the feed stream preferably contains a reduced content of $R_1$—O-secondary-$R_2$. As mentioned above, this is desirable because some of the $R_1$—O-secondary-$R_2$ that enters the decomposition zone may decompose to the $R_2$-normal olefin and ultimately contaminate the $R_2$-isoolefin product. However, it is usually unattractive to remove the $R_1$—O-secondary-$R_2$ in the feed stream by conventional distillation, in part because the flow rate of the feed stream is relatively large compared to other process streams in the decomposition process, because the relative volatilities of the $R_1$—O-secondary-$R_2$ and the $R_1$—O-tertiary-$R_2$ are comparatively close, and because the feed stream contains a relatively high ratio of $R_1$—O-tertiary-$R_2$/$R_1$—O-secondary $R_2$. The content of $R_1$—O-secondary-$R_2$ in the feed stream from an etherification process of the prior an is largely determined by the selectivity of the reaction conditions in the etherification process and, therefore, is usually not a matter of choice of the practitioner of the decomposition process.

Also, where the feed stream is obtained by olefin etherification processes of the prior art, the feed stream may contain from about 200 to about 700 ppm by weight $R_2$-normal olefins. Where the $R_2$-normal olefin impurity requirement of the $R_2$-isoolefin product is stringent, the feed stream preferably contains a reduced content of $R_2$-normal olefins, which can be removed from the feed stream by conventional distillation.

The feed stream is vaporized and contacted with a decomposition catalyst in a decomposition zone. Decomposition catalysts are well known in the prior art as exemplified by U.S. Pat. Nos. 4,320,232 and 4,570,026. Examples of suitable decomposition catalysts are ion exchangers in the hydrogen form such as nuclear-sulfonated, crosslinked styrene-divinylbenzene copolymers, acidic alumina silicate, solid phosphoric acid catalysts such as polyphosphoric acid on a solid carrier such as silica gel, acid metal sulfates such as sodium bisulfate on a silica gel carrier, and metal hydrogen phosphates such as aluminum phosphate. The preferred decomposition catalyst is acidic alumina silicate. What is important is that catalysts for decomposition are well known to those skilled in the decomposition art and need not be described here in great detail. The nature of the decomposition catalyst is not critical to the success of the invention. Although some commercially-available decomposition catalysts are more selective than others at maximizing the yield of $R_2$-isoolefins and minimizing the yield of $R_2$-normal olefins, it is believed that $R_2$-normal olefins are formed from $R_1$—O-secondary-$R_2$ at least to a small extent at suitable decomposition conditions in the presence of most if not all commercially available decomposition catalysts. Since it is an economic advantage to operate the decomposition zone at conditions that produce a high yield of the $R_2$-isoolefins from the $R_1$—O-tertiary-$R_2$, the $R_2$-normal olefins are produced at least to a small extent in most if not all commercial decomposition zones.

The conditions of the decomposition zone are effective to decompose the $R_1$O-tertiary-$R_2$ to the $R_2$-isoolefin. The decomposition zone preferably contains at least one fixed bed reactor. The liquid hourly space velocity is generally from about 1 to about 50 $hr^{-4}$, and preferably from about 4 to about 8 $hr^{-4}$. Liquid hourly space velocity is defined herein as the feed rate as a liquid phase in units of volume per hour divided by the catalyst quantity in the same units of volume, so that the units are $hr^{-4}$. The temperature of the decomposition is dependent on the liquid hourly space velocity and the nature of the decomposition catalyst, but it is generally from about 50° to about 400° C., and preferably from about 150° to about 300° C. The pressure of the decomposition may be carded out at atmospheric pressure or at a pressure above atmospheric pressure, but it is generally from about 1 to about 25 barg, and preferably from about 4 to about 10 barg.

The decomposition conditions may be effective to decompose the $R_1$—O-secondary-$R_2$ to the $R_2$-normal olefin. However, the invention is not limited to conditions that effect the decomposition of the $R_1$—O-secondary-$R_2$. For example, in applications where the $R_1$—O-secondary-$R_2$ does not decompose, the invention may be used to prevent the $R_1$—O-secondary-$R_2$ from accumulating in the decomposition zone or to recover a higher yield of the $R_1$—O-secondary-$R_2$ as a separate by-product.

The effluent of the decomposition reactor, which is referred to herein as the decomposition effluent stream, contains principally $R_2$-isoolefin and $R_1$—OH. Typically, it may also contain $R_1$—O-tertiary-$R_2$ and $R_2$-normal olefin. From the previous description, generally not more than about 10–15% by weight of the $R_1$—O-secondary-$R_2$ that enters the decomposition zone decomposes to $R_2$-normal olefins. Therefore, the effluent of the decomposition reactor also contains $R_1$—O-secondary-$R_2$. The relative concentration of $R_1$—O-tertiary-$R_2$ and $R_1$—O-secondary-$R_2$ in the decomposition effluent stream can also be expressed in terms of the ratio of $R_1$—O-tertiary-$R_2$/$R_1$—O-secondary-$R_2$, and for the decomposition effluent stream this ratio is relatively low in comparison with the feed stream. The decomposition effluent stream passes into a first separation zone, from which are recovered a product stream containing $R_2$-isoolefin and a first recycle stream containing $R_1$—O-secondary-$R_2$. This separation is preferably done by distillation, and usually at least one distillation column is employed. The column separates the decomposition effluent stream into a product stream containing $R_2$-isoolefin and $R_2$-normal olefin and a first recycle stream containing $R_1$—OH, $R_1$—O-secondary-$R_2$, and $R_1$—O-tertiary-$R_2$. Typically, a product stream of at least 95% $R_2$-isoolefin can be obtained without any special measures, prior to water washing. The $R_2$-normal olefin content of the product stream is generally not more than 800 ppm by weight, preferably not more than 300 ppm by weight. The relative concentrations of the $R_1$—O-tertiary-$R_2$ and of the $R_1$—O-secondary-$R_2$ in the first recycle stream are like those in the decomposition effluent stream, by which it is meant that the ratio of $R_1$—O-tertiary-$R_2$/$R_1$—O-secondary-$R_2$ in the first recycle stream is relatively low in comparison with the feed stream.

The first recycle stream passes into a second separation zone which operates at conditions effective to separate the entering $R_1$—O—$R_2$ into a drag stream containing a first concentration of $R_1$—O-secondary-$R_2$ and a second recycle stream containing a second concentration of $R_1$—O-secondary-$R_2$. Typically, a recirculating stream containing $R_1$—OH is also recovered and it may be advantageously recycled to an etherification zone where present. These distillate separations can be obtained without any special measures, and usually at least one distillation column is employed, and preferably either one or two distillation columns are employed. Where two distillation columns are employed, the first column produces an overhead stream containing $R_1$—O-secondary-$R_2$ and $R_1$—O-tertiary-$R_2$ and the recirculating stream as a bottom stream, and the second column separates the first column overhead stream into the drag stream and the second recycle stream. Where one distillation column is employed, the column produces the second recycle stream as an overhead stream, the drag stream as a side-cut product, and the recirculating stream as a bottom product. The second recycle stream is recycled to the decomposition zone, and the drag stream is recovered and may be used as an anti-knock additive in gasoline.

The first concentration may be generally from about 1 to about 5% by weight of $R_1$—O-secondary-$R_2$, and the second concentration may be generally from about 0.02 to about 2.0% by weight $R_1$—O-secondary-$R_2$. These ranges are illustrative only and do not limit the invention in any way. The first concentration must be greater than the second concentration in order to concentrate the $R_1$—O-secondary-$R_2$ in the drag stream thereby removing it and preventing its decomposition to $R_2$-normal olefin. The greater the first concentration relative to the second concentration, the greater is the removal of the $R_1$—O-secondary-$R_2$ from the first recycle stream. It is believed that benefits in accord with the invention can be achieved from removing as little as 5% by weight of the $R_1$—O-secondary-$R_2$ in the first recycle stream. In a preferred embodiment of the invention, 30% by weight of the $R_1$—O-secondary-$R_2$ in the first recycle stream is removed.

The $R_1$—O-secondary-$R_2$ aside, the second recycle stream may contain $R_1$—O-tertiary-$R_2$, which is advantageously recycled to the decomposition zone. However, the invention is not limited by a requirement that $R_1$—O-tertiary-$R_2$ be present in the second recycle stream. For example, the second recycle stream may contain an inert diluent that is recycled through the decomposition zone and from which the $R_1$—O-secondary-$R_2$ can be advantageously and selectively separated. For example, such a diluent may be used for the purpose of improved heat transfer in the decomposition reactor.

The second recycle stream may also contain $R_1$—OH. However, the content of $R_1$—OH in the second recycle stream is preferably minimized because it is more advantageously recycled to an etherification zone and also because its presence in the decomposition reactor may lead to the formation of $R_1$—O—R.

The operating conditions of the first separation zone and the second separation zone can be optimized by those skilled in the art of distillation to operate over wide ranges, which are expected to include common conditions. Therefore, an embodiment of the invention includes the first separation zone contained in a common separation vessel with the second separation zone. However, it is expected that such an embodiment may have the disadvantage of increasing the mount of $R_1$—OH that is recycled to the decomposition reactor and thereby increasing the formation of $R_1$—O—$R_1$.

In a more limited embodiment, the invention is a process especially well-suited to isolating isoolefins from mixtures of hydrocarbons of the same carbon number. The feed stream to the subject process of the second broad embodiment is a $R_2$-hydrocarbon mixture containing $R_2$-isoolefin. The majority of the description of the second broad embodiment is presented in terms of the isolation of isobutene from mixtures of $C_4$ hydrocarbons by reaction with methanol to form MTBE and the subsequent decomposition of the MTBE back to isobutene since these are the preferred feed materials and the commercially predominant reaction. However, this description is not intended to limit the scope of the invention in any way. The feed stream to the subject process is a mixture of $C_4$ hydrocarbons. The feed stream may contain other hydrocarbons but preferably this feed stream will contain less than 10 mole percent total $C_5+$ and $C_3-$ hydrocarbons. That is, preferably over 90 mole percent of the hydrocarbons in the feed stream will be $C_4$ hydrocarbons. The feed stream contains the desired product isoolefin, that is isobutene, and the feed stream preferably contains at least 10% by weight isobutene. Suitable mixtures of $C_4$ hydrocarbons are normally produced in commercial quantities by a cracking process such as thermal cracking or fluidized catalytic cracking (FCC). In the latter instance the $C_4$ olefins are a valuable by-product of the FCC process typically operated to produce gasoline and other distillates in a petroleum refinery. Another potential source of the feed stream is a catalytic dehydrogenation zone operating on a $C_4$ feed stream.

The feed stream may contain butadiene, but removal of the butadiene prior to the subject process is preferred. Therefore, it is preferred that, if the feed stream contains butadiene, a selective hydrogenation reaction zone be present at some point within the process flow. For instance, the selective hydrogenation reaction zone could be located on the feed stream. Where the feed stream is a mixture of $C_4$ hydrocarbons, the operation of the selective hydrogenation zone and the catalyst employed within this zone affect the normal butene isomer distribution, but it is not expected to affect the isobutene content of the feed stream. However, where the feed stream is a mixture of $C_5$ hydrocarbons, the 3-methyl 1-butene isoolefin present is expected to be isomerized to 2-methyl 2-butene and 2-methyl 1-butene isomers, thereby increasing the yield of these isoolefins. Catalyst and processing conditions for selective hydrogenation are well known to those skilled in the art. For instance, hydrogenation for this purpose is described in the article starting at page 51 of the March 1985 edition of "Hydrocarbon Processing." Suitable catalysts, operating conditions and procedures are described in U.S. Pat. Nos. 3,480,531; 4,551,443; and 4,571,442. The preferred catalyst comprises either palladium or nickel on an alumina support. The preferred catalyst contains generally from about 0.3 to 1.5 weight percent active metal in a sulfided state. Further details on suitable catalysts may be obtained from U.S. Pat. Nos. 3,472,763 and 4,440,956.

Etherification processes have been constructed and proposed for the production of a variety of $R_1$—O—$R_2$, including MTBE. Large amounts of MTBE are being produced for use as anti-knock additives in lead-free gasoline. The etherification zone may take many different forms including a catalytic-reaction-with-distillation zone but it is preferably similar to that described in U.S. Pat. No. 4,219,678 and the previously cited paper by Obenaus et al. The feed stream and methanol pass into an etherification zone and contact an acidic catalyst at etherification conditions. A wide range of materials is known to be effective as etherification catalysts for the preferred reactants including mineral acids such as sulfuric acid, boron trifluoride, phosphoric acid on kieselguhr, phosphorus-modified zeolites, heteropolyacids, and various sulfonated resins. The use of a sulfonated solid resin catalyst is preferred. These resin-type catalysts include the reaction products of phenol-formaldehyde resins and sulfuric acid and sulfonated polystyrene resins including those cross-linked with divinylbenzene. Further information on suitable etherification catalysts may be obtained by reference to U.S. Pat. Nos. 2,480,940; 2,922,822; and 4,270,929 and the previously cited etherification references. What is important is that catalysts for etherification are well known to those skilled in the etherification art and need not be described here in great detail. The nature of the etherification catalyst is not critical to the success of the invention and is largely a matter of choice to be made by the practitioner.

A broad range of etherification promoting conditions include a superatmospheric pressure sufficient to maintain the reactants as a liquid phase, generally below about 15 barg, and a temperature generally between about 30° C. and about 100° C., and preferably between about 50° C. and about 100° C. The etherification zone may comprise one or more reactors. The molar ratio of feed methanol to isobutene should normally be maintained in the broad range of from about 1:1 to about 2:1, preferably from about 1.1:1 to about 1.5:1.

The effluent of the etherification zone, referred to herein as the etherification effluent stream, contains MTBE in addition to $C_4$ hydrocarbons. The etherification effluent stream may contain by-product $C_4$ hydrocarbon oligomers, such as diisobutene and triisobutene. The etherification effluent stream will also contain methyl secondary-butyl ether (MSBE). Without limiting this invention in any way, it is believed that MSBE is formed from an etherification reaction between normal butene in the feed and methanol. However, the MSBE may be formed by other reactants and reactions, and the particular nature of the reactions and reactants is not critical to the success of the invention. Although some commercially available etherification catalysts are more selective than others at minimizing the formation of MSBE, it is believed that MSBE is formed at least to a small extent at suitable etherification conditions in the presence of most if not all commercially available etherification catalysts. Since it is an economic advantage to operate the etherification zone at conditions that produce a high yield of the MTBE from isobutene, MSBE is produced at least to a small extent in most if not all commercial etherification zones.

The etherification effluent stream passes into a first separation zone, from which are recovered a first product stream containing the $C_4$ hydrocarbons and an etherification product stream containing MTBE and MSBE. Where the etherification effluent stream contains $C_4$ hydrocarbon oligomers, a drag stream containing the $C_4$ hydrocarbon oligomers may be recovered from the first separation zone and used in gasoline blending. This separation is preferably done by distillation, and usually at least one distillation column is employed.

The etherification product stream passes to a decomposition zone and subsequently to two separation zones. These zones are described above in the first embodiment of invention, and need not be described here in great detail. The decomposition effluent stream passes into a second separation zone, from which are recovered a second product stream containing isobutene and a first recycle stream containing MSBE. The first recycle stream passes into a third separation zone, from which are recovered a drag stream containing a first concentration of MSBE and a second recycle stream containing a second concentration of MSBE. The first concentration must be greater than the second concentration. The second recycle stream may contain methanol and MTBE. The second recycle stream may be recycled to the decomposition zone or the etherification zone, but the first separation zone is preferred. This is because the first separation zone can be operated to separate the methanol and thereby minimize its entry into the decomposition reactor where it may either react subsequently to dimethyl ether or inhibit the decomposition of MTBE, and also because the recycling of MTBE to the etherification zone may inhibit the formation of MTBE therein.

In a preferred variation of this more limited embodiment, the second product stream passes to a fourth separation zone, which removes essentially all of the dimethyl ether contained in the second product stream. A third product stream containing isobutene and a substantially reduced concentration of dimethyl ether is recovered. The dimethyl ether is recycled in a third recycle stream to the etherification zone, and it is ultimately recovered from the first separation zone in the first product stream. The fourth separation zone typically comprises at least one distillation column and the separation required for the isobutene product can be obtained without any special measures.

A complete operation of the process can be more fully understood from a process flow for a preferred embodiment.

Referring now to FIG. 1, a feed stream, comprising an admixture of $C_4$ hydrocarbons including isobutene and normal butene is charged in line 10. The $C_4$ hydrocarbons are combined with a stream of recycle dimethyl ether from line 36 and charged in line 12. The $C_4$ hydrocarbons and the dimethyl ether are admixed with methanol from line 16 and passed through line 14 into an etherification zone 20. Inside the etherification zone, which comprises at least one etherification reactor, the $C_4$ hydrocarbons and the methanol are contacted in the presence of an etherification catalyst at conditions which effect principally the etherification of isobutene to MTBE, but also, as a side reaction, the production of MSBE. There is thus produced an etherification effluent stream carried by line 22 which comprises a mixture of MTBE, MSBE, dimethyl ether, methanol, and $C_4$ hydrocarbons. The etherification effluent stream enters a debutanizer column 24. A debutanizer overhead product stream containing $C_4$ hydrocarbons, methanol, and dimethyl ether passes through line 28 to a raffinate water wash column 30. A debutanizer bottom product stream containing $C_4$ oligomers, where present as other by-products of reactions that occur in the etherification zone, passes through line 50 and is recovered for use in, for example, gasoline blending.

A debutanizer sidecut product stream containing a mixture of MTBE and MSBE passes through line 48 to decomposition zone 52. Inside the decomposition zone, which comprises at least one decomposition reactor, MTBE and MSBE are contacted in the presence of a decomposition catalyst at conditions which principally effect the decomposition of MTBE to isobutene, but also, as a side-reaction, the decomposition of MSBE to normal butene. There is thus produced a decomposition effluent stream carried by line 56 which comprises a mixture of MTBE, MSBE, methanol, isobutene, and normal butene. Dimethyl ether may also be present in the decomposition stream as a by-product of side reactions that occur in the decomposition reactor. The etherification effluent stream enters an isobutene column 58. An isobutene column overhead product stream containing isobutene, normal butene, methanol, and dimethyl ether passes through line 70 to isobutene water wash column 72. An isobutene column bottoms product stream containing methanol, MTBE, and MSBE passes through line 60 to azeotrope column 62. An azeotrope column overhead product stream containing MTBE, MSBE, and methanol passes through line 66 to a rerun column 44. An azeotrope column bottom product stream containing methanol passes through line 64, combines with a stream of recovered methanol in line 86 from a methanol column 88, passes through line 54, combines with make-up methanol charged through line 18, and ultimately recycles to the etherification zone 20 through the line 16 and the line 14.

The rerun column 44 removes at least a portion of the MSBE in the azeotrope column overhead product stream in a rerun column bottoms product stream containing MSBE. The rerun column bottoms stream passes through line 46 and is recovered, for example, for gasoline blending. A rerun column overhead product stream containing MSBE, MTBE, and methanol passes through line 26 and enters the debutanizer column 24.

Methanol is recovered by water washing from both the debutanizer overhead product stream, which passes through the line 28, and the isobutene column overhead product stream, which passes through the line 70. The methanol column 88 produces a methanol column bottoms stream containing water that passes through line 90. A water bleed stream is bled through line 84 to prevent the accumulation of contaminants in the wash water. The wash water stream splits into two streams, one that passes to the isobutene water wash column 72 through line 78, and one that passes to the raffinate water wash column 30 through line 42 and line 38. A make-up water stream is charged through line 40 to compensate for the water bleed stream. The raffinate water wash column overhead stream containing $C_4$ hydrocarbons and dimethyl ether passes on to downstream processing through line 34. The raffinate water wash column bottom stream containing methanol and water passes through line 32 and line 68 to the methanol column 88. The isobutene water wash column overhead stream containing isobutene passes through line 76 to a stripper column 80, and the isobutene water wash column bottoms stream containing water and methanol passes through line 74, joins with the raffinate water wash column bottom stream, and passes through the line 68 to the methanol column 88.

The stripper column 80 separates the isobutene water wash column overhead stream into a stripper column overhead stream and a stripper column bottoms stream. The stripper column overhead stream which contains dimethyl ether passes through the line 36, combines with the $C_4$ hydrocarbon feed stream, and is ultimately recycled to the etherification zone through the line 12 and the line 14. The stripper column bottom stream contains isobutene and is recovered as a product steam through line 82.

The two following examples illustrate the benefits of the invention on the impurity and yield of the product isobutene in a decomposition process. These examples are based on essentially the same feed stream composition, conventional engineering calculations, and scientific decomposition yield predictions.

EXAMPLE 1

Example 1 illustrates a variation of the process flow of FIG. 1, in which the rerun column overhead product stream, which passes through the line 26, is recycled to the decomposition zone 52 instead of to the debutanizer column 24.

Table 1 shows the composition of the streams associated with the decomposition zone. Referring to the isobutene column overhead product stream, which passes through line 70 and is shown prior to water washing or dimethyl ether separation, the impurity is 432 ppm by weight and the yield is 98.2% by mole.

passes through the line 66 and is recycled directly to the decomposition zone 52, without the rerun column 44. To remove MSBE from the process, a bleed stream consisting of a portion of the azeotrope column overhead product stream is withdrawn from between the azeotrope column 62 and the decomposition zone 52.

Table 2 shows the compositions of the streams associated with the decomposition zone. Referring to the isobutene column overhead product stream, which passes through line 70 and is shown prior to water washing or dimethyl ether separation, the impurity is 458 ppm by weight and the yield is 93.5% by mole.

Therefore, the invention as illustrated in Example 1 produces not only a lower impurity but also a higher yield of the product isobutene than Example 2.

TABLE 1

| | STREAM: | | | | |
|---|---|---|---|---|---|
| COMPOSITION: | Etherification Product | Isobutene Column Overhead Product | Azeotrope Column Bottom Product | Rerun Column Overhead Product | Rerun Column Bottom Product |
| Water, wt. % | — | 0.40 | — | — | — |
| Dimethyl Ether, wt. % | — | 0.39 | — | — | — |
| Isobutene, wt. % | — | 95.38 | — | — | — |
| Normal Butene, wppm | 94 | 432 | — | — | — |
| Normal Butane, wppm | 94 | 144 | — | — | — |
| Methanol, wt. % | 0.003 | 3.77 | 97.67 | 15.89 | — |
| Tert-Butyl Alcohol, wt. % | 0.66 | — | — | — | — |
| MTBE, wt. % | 99.19 | — | — | 83.66 | 97.22 |
| $C_8$, wt. % | 0.05 | — | 2.33 | — | — |
| MSBE, wt. % | 0.075 | — | — | 0.45 | 2.78 |
| TOTAL, wt. % | 100 | 100 | 100 | 100 | 100 |

EXAMPLE 2

Example 2 illustrates a variation of the process flow in FIG. 1 that is without the benefit of the invention. In this example, the azeotrope column overhead product stream

TABLE 2

| COMPOSITION: | Etherification Product | Isobutene Column Overhead Product | Azeotrope Column Bottom Product | Azeotrope Column Overhead Product | Bleed |
|---|---|---|---|---|---|
| Water, wt. % | — | 0.42 | — | | |
| Dimethyl Ether, wt. % | — | 0.43 | — | | |
| Isobutene, wt. % | — | 95.32 | — | | |
| Normal Butene, wppm | 94 | 458 | — | | |
| Normal Butane, wppm | 94 | 151 | — | | |
| Methanol, wt. % | 0.003 | 3.77 | 97.88 | 15.00 | 15.00 |
| Tert-Butyl Alcohol, wt. % | 0.65 | — | | | |
| MTBE, wt. % | 99.20 | — | — | 84.39 | 84.39 |
| $C_8$, wt. % | 0.05 | — | 2.12 | | |
| MSBE, wt. % | 0.075 | — | — | 0.61 | 0.61 |
| TOTAL, wt. % | 100 | 100 | 100 | 100 | 100 |

Examples 1 and 2 illustrate the benefit of passing the etherification product stream through the decomposition zone and thereby concentrating the MSBE relative to the MTBE, and how this benefit can subsequently be used to an advantage in separating MSBE and MTBE. Table 2 shows the etherification product stream contains 99.20 wt-% MTBE and 0.075 wt-% MSBE, meaning that the ratio of MTBE to MSBE is 1,323. This etherification product stream is passed to the decomposition zone and then to the azeotrope column. The azeotrope column overhead stream contains 84.39 wt-% MTBE and 0.61 wt-% MSBE, meaning that the ratio of MTBE to MSBE is 138, which is significantly lower than the ratio in the etherification product stream. In other words, the concentration of MSBE relative to MTBE has increased by nearly a factor of 10 from the etherification product stream to the azeotrope column overhead stream. In the present invention, it is the azeotrope column overhead stream that is passed to the rerun column, which removes a drag stream containing a relatively-high concentration of MSBE. The rerun column of the present invention is significantly less expensive to build and operate than columns used by processes of the prior art to separate MSBE and MTBE in the etherification product stream.

What is claimed is:

1. A process for producing $R_2$-isoolefins, where $R_2$ is one of a $C_4$ and a $C_5$ alkyl group, from a feed stream comprising $R_1$—O-tertiary-$R_2$ and $R_1$—O-secondary-$R_2$, where $R_1$ is an alkyl group comprising from 1 to 5 carbon atoms, which process comprises the steps of:

(a) passing a feed stream comprising an $R_1$—O-tertiary-$R_2$ and an $R_1$—O-secondary-$R_2$ and having a first ratio of $R_1$—O-tertiary-$R_2/R_1$—O-secondary-$R_2$ into a decomposition zone maintained at decomposition conditions effective to decompose said $R_1$—O-tertiary-$R_2$ to an $R_2$-isoolefin corresponding to said $R_2$ and recovering therefrom a decomposition effluent stream comprising said $R_2$-isoolefin and said $R_1$—O-secondary-$R_2$;

(b) passing at least a portion of said decomposition effluent stream into a first separation zone operated at conditions effective to separate said portion of said decomposition effluent stream into a product stream comprising said $R_2$-isoolefin and a first recycle stream comprising said $R_1$—O-secondary-$R_2$;

(c) passing at least a portion of said first recycle stream having a second ratio of $R_1$—O-tertiary-$R_2/R_1$—O-secondary-$R_2$ that is less than said first ratio into a second separation zone operated at conditions effective to selectively separate said portion of said first recycle stream into a drag stream having a first concentration of said $R_1$—O-secondary-$R_2$ and a second recycle stream having a second concentration of said $R_1$—O-secondary-$R_2$ that is less than said first concentration;

(d) recycling at least a portion of said second recycle stream to said decomposition zone; and (e) withdrawing said drag stream from said process.

2. The process of claim 1 further characterized in that said second recycle stream comprises $R_1$—O-tertiary-$R_2$.

3. The process of claim 1 further characterized in that said decomposition conditions are effective to decompose said $R_1$—O-secondary-$R_2$ to a $R_2$-normal olefin.

4. The process of claim 3 further characterized in that said product stream has not more than 800 ppm by weight of said $R_2$-normal olefin.

5. The process of claim 1 further characterized in that at least 5% by weight of said $R_1$—O-secondary-$R_2$ in said first recycle stream is withdrawn from the process.

6. The process of claim 1 further characterized in that at least 30% by weight of said $R_1$—O-secondary-$R_2$ in said first recycle stream is withdrawn from the process.

7. The process of claim 1 where said $R_1$ is a methyl group and said $R_2$ is either a butyl group or a pentyl group.

8. The process of claim 1 further characterized in that said decomposition zone contains a decomposition catalyst selected from the group consisting of ion exchangers in the hydrogen form, crosslinked styrene-divinylbenzene copolymers, solid phosphoric acid on a solid carrier, acid metal sulfates on a silica gel carrier, and metal hydrogen phosphates.

9. The process of claim 1 where said first separation zone comprises at least one distillation column.

10. The process of claim 1 where said second separation zone comprises at least one distillation column.

11. The process of claim 1 further characterized in that said first separation zone and said second separation zone are contained in a common separation vessel.

12. A process for obtaining isobutene from a $C_4$ hydrocarbon mixture comprising isobutene, which process comprises the steps of:

(a) passing a $C_4$ hydrocarbon mixture comprising isobutene and an $R_1$—OH, where $R_1$ is an alkyl group comprising from 1 to 5 carbon atoms, into an etherification zone maintained at etherification conditions effective to etherify said isobutene and recovering therefrom an etherification effluent stream comprising $C_4$ hydrocarbons, an $R_1$—O-tertiary-$C_4$ corresponding to said $R_1$, and an $R_1$—O-secondary-$C_4$ corresponding to said $R_1$;

(b) passing at least a portion of said etherification effluent stream into a first separation zone operated at conditions effective to separate said portion of said etherification effluent stream into a first product stream comprising $C_4$ hydrocarbons and an etherification product stream comprising said $R_1$—O-tertiary-$C_4$ and said $R_1$—O-secondary-$C_4$;

(c) passing at least a portion of said etherification product stream having a first ratio of $R_1$—O-tertiary-$C_4$/$R_1$—O-secondary-$C_4$ into a decomposition zone maintained at decomposition conditions effective to decompose said $R_1$—O-tertiary-$C_4$ to isobutene and recovering therefrom a decomposition effluent stream comprising isobutene and said $R_1$—O-secondary-$C_4$;

(d) passing at least a portion of said decomposition effluent stream into a second separation zone operated at conditions effective to separate said portion of said decomposition effluent stream into a second product stream comprising isobutene and a first recycle stream comprising said $R_1$—O-secondary-$C_4$;

(e) passing at least a portion of said first recycle stream having a second ratio of $R_1$—O-tertiary-$C_4$/$R_1$—O-secondary-$C_4$ that is less than said first ratio into a third separation zone operated at conditions effective to selectively separate said portion of said first recycle stream into a first drag stream having a first concentration of said $R_1$—O-secondary-$C_4$ and a second recycle stream having a second concentration of said $R_1$—O-secondary-$C_4$ that is less than said first concentration;

(f) recycling at least a portion of said second recycle stream to at least one zone selected from the group consisting of said etherification zone, said first separation zone, and said decomposition zone; and (g) withdrawing said first drag stream from said process.

13. The process of claim 12 further characterized in that said second recycle stream comprises $R_1$—O-tertiary-$C_4$.

14. The process of claim 12 further characterized in that said decomposition conditions are effective to decompose said $R_1$—O-secondary-$C_4$ to a normal butene.

15. The process of claim 14 further characterized in that said second product stream has not more than 800 ppm weight of normal butene.

16. The process of claim 12 further characterized in that said second product stream comprises a $R_1$—O—$R_1$.

17. The process of claim 16 further characterized in that at least a portion of said second product stream is passed into a fourth separation zone operated at conditions effective to separate said portion of said second product stream into a third product stream comprising isobutene and a third recycle stream comprising said $R_1$—O—$R_1$, and at least a portion of said third recycle stream is recycled to said etherification zone.

18. The process of claim 12 further characterized in that said etherification effluent stream contains a $C_4$ hydrocarbon oligomer.

19. The process of claim 18 further characterized in that said $C_4$ hydrocarbon oligomer is diisobutene.

20. The process of claim 18 further characterized in that a second drag stream containing said $C_4$ hydrocarbon oligomer is recovered from said first separation zone.

21. The process of claim 12 further characterized in that at least 5% by weight of said $R_1$—O-secondary-$C_4$ in said first recycle stream is withdrawn from the process.

22. The process of claim 12 further characterized in that at least 30% by weight of said $R_1$—O-secondary-$C_4$ in said recycle stream is withdrawn from the process.

23. The process of claim 12 where $R_1$ is a methyl group, said $R_1$—O-tertiary-$C_4$ is methyl tertiary-butyl ether, and said $R_1$—O-secondary-$C_4$ is methyl secondary-butyl ether.

24. The process of claim 12 further characterized in that said decomposition zone contains a decomposition catalyst selected from the group consisting of ion exchangers in the hydrogen form, crosslinked styrene-divinylbenzene copolymers, solid phosphoric acid on a solid carrier, acid metal sulfates on a silica gel carrier, and metal hydrogen phosphates.

25. The process of claim 12 where said second separation zone comprises at least one distillation column.

26. The process of claim 12 where said third separation zone comprises at least one distillation column.

27. The process of claim 12 further characterized in that said second separation zone and said third separation zone are contained in a common separation vessel.

* * * * *